(12) United States Patent
Welch

(10) Patent No.: US 6,171,449 B1
(45) Date of Patent: Jan. 9, 2001

(54) CASCADE REBOILING OF ETHYLBENZENE/STYRENE COLUMNS

(75) Inventor: Vincent A. Welch, Medway, MA (US)

(73) Assignee: Washington Group International, Inc., Boise, ID (US)

( * ) Notice: Under 35 U.S.C. 154(b), the term of this patent shall be extended for 0 days.

(21) Appl. No.: 09/100,433

(22) Filed: Jun. 19, 1998

(51) Int. Cl.$^7$ ............................... B01D 3/42; C07C 7/04
(52) U.S. Cl. ...................... 202/154; 202/155; 202/172; 202/173; 203/1; 203/25; 203/73; 203/78; 203/80; 203/DIG. 8; 203/DIG. 9; 585/401; 585/440; 585/441; 585/805; 585/910
(58) Field of Search .................. 203/25, 27, DIG. 8, 203/DIG. 9, 1, 73, 80, 78; 585/401, 402, 440, 441, 805, 804, 910, 914; 202/154, 173, 172, 155

(56) References Cited

U.S. PATENT DOCUMENTS

| | | | |
|---|---|---|---|
| 3,515,647 | 6/1970 | Van Tassell et al. | 203/49 |
| 3,702,346 | 11/1972 | Kellar | 260/669 |
| 3,775,970 | 12/1973 | Strazik et al. | 260/669 |
| 3,801,664 | 4/1974 | Blytas | 260/669 |
| 3,904,484 | 9/1975 | King | 203/52 |
| 4,113,787 | * 9/1978 | Ward | 585/441 |
| 4,615,769 | * 10/1986 | Horigome et al. | 203/26 |
| 4,628,136 | 12/1986 | Sardina | 585/441 |
| 4,824,527 | * 4/1989 | Erickson | 203/25 |
| 5,386,075 | * 1/1995 | Keil et al. | 585/800 |
| 5,573,645 | * 11/1996 | Pickering, Jr. | 203/25 |

* cited by examiner

Primary Examiner—Virginia Manoharan
(74) Attorney, Agent, or Firm—David Silverstein; Andover-IP-Law

(57) ABSTRACT

Apparatus and process are disclosed for the distillation separation of styrene monomer from ethylbenzene utilizing a split feed to two distillation columns in conjunction with cascade reboiling utilizing thermal energy from the overhead of one column to supply heat to the second.

11 Claims, 1 Drawing Sheet

CASCADE REBOILING OF ETHYLBENZENE/STYRENE COLUMNS

BACKGROUND OF THE INVENTION

Conventional processes for styrene manufacture which are in general commercial use employ ethylbenzene as the starting material or immediate precursor of the styrene product. In a large majority of these processes, the ethylbenzene is catalytically dehydrogenated to yield the desired styrene product. Typically, the conversions of ethylbenzene to styrene obtained with these processes is far from complete, typically at a rate of about 50–70% per pass across the reactor. Therefore, in normal operations, the dehydrogenation reaction product will be a mixture containing substantial portions of styrene and ethylbenzene as well as minor amounts of reaction by-products and impurities such as benzene, toluene, light ends including hydrogen, methane and ethylene, and heavy ends. The unreacted ethylbenzene must then be recovered and separated from the styrene product prior to recycle to the dehydrogenation reaction system. Thus, the mixture of light components, ethylbenzene, styrene and heavies is typically fed to a distillation train for SM product purification and EB recovery. The general practice is to accomplish these purifications by distillation, as taught for example in U.S. Pat. No. 3,904,484 (King) which patent is incorporated herein by reference.

The separation of the desired styrene product from the light ends, heavy ends, benzene and toluene is relatively easy, being accomplished by conventional sequential distillations. To separate the various components, the distillation section of a styrene plant will typically consist of at least three independent column systems. The column first in the series recovers the light components such as benzene and toluene (B/T Column), the second column recovers unreacted ethylbenzene (EB/SM Column), and the last column distills heavies from the finished styrene product (Finishing Column). Separation by distillation of the styrene monomer (SM) from the unreacted ethylbenzenie (EB), however, presents a considerably more difficult problem due primarily to their close similarity in volatility. First of all, the boiling points of ethylbenzene and styrene, 136.15° C. at 760 mm Hg and 146.0° C. at 760 mm Hg, respectively, are so close as to make sepertion by fractional distilled difficult. Conventionally, this EB/SM separation has been accomplished by distillation under vacuum conditions in large, sophisticated, and expensive distillation columns due to the large number of theoretical plates required to effect a good separation. Thus, conventionally, unreacted ethylbenzene from the dehydrogenation reaction section is separated from styrene in a single distillation column. In the standard design, a large number of theoretical stages (between 85 and 100) is required to effect the required separation. This single unit operation accounts for between 70 and 80 percent of the total distillation section heat input. In a typical plant, the separation of unreacted ethylbenzene from styrene product accounts for approximately 20–30% of the plant's steam consumption. If the energy consumption required for separating ethylbenzene from styrene in a 500,000 MTA styrene monomer plant could be reduced 50%, the savings would be on the order of $700,000/year.

Even under vacuum conditions, a polymerization inhibitor is added to the mixture because of the tendency of the styrene product to polymerize at the time and temperature conditions required to effect the separation by distillation. Styrene polymerizes to a measurable degree even at room temperature. The key which allows styrene distillation to be commercially practiced is the use of chemical additives referred to as polymerization inhibitors. To minimize styrene polymerization, and the associated fouling of equipment and need to process a highly viscous product stream, commercial styrene distillation is nearly always carried out under vacuum conditions (e.g., operating with a column overhead pressure of about 40 to 120 mm Hg abs). In the temperature range utilized by commercial styrene units, the rate of polymerization of uninhibited styrene doubles for every 10° C. temperature increase. Also, to achieve the larger number of stages required to effect the separation, currently either structured or random dump packing materials are used as the internal vapor/liquid contacting medium. Packing materials intrinsically have much lower pressure drop compared to standard distillation trays. With packing, the lower pressure drop allows the column to operate with a comparatively lower bottoms temperature. As a result of these various process difficulties, costs, and limitations, however, considerable incentive has existed for many years to develop alternative means of effecting this separation which could be more viable from either or both economic and ease of operation standpoints. A number of patents have attempted to address these problems in a variety of ways.

Thus, U.S. Pat. No. 3,515,647 (Van Tassell et al.) teaches a process for purifying styrene via a distillation scheme having associated therewith a wiped wall thin film evaporator to maximize recovery of styrene from the residue material. Styrene in a purity of at least 99% by weight is recovered as a separate product stream.

In U.S. Pat. No. 3,702,346 (Kellar), a process for the steam dehydrogenation of ethylbenzene to styrene, the selectivity of the dehydrogenation reaction is improved by maintaining the reactor products settler, wherein condensed reactor products are separated, at a pressure less than atmospheric. This improvement in selectivity in turn somewhat reduces the costs and difficulties of the subsequent styrene separation.

U.S. Pat. No. 3,776,970 (Strazik et al.) describes a process in which styrene is separated from organic mixtures comprising styrene and ethylbenzene by contacting the mixture against one side of a polyurethane elastomer membrane under pervaporation permeation conditions and withdrawing at the other side a vaporous mixture having increased styrene concentration. The polyurethane elastomer contains polyether or polyester groupings.

U.S. Pat. No. 3,801,664 (Blytas) teaches another process in which styrene is separated from ethylbenzene in high yield and purity. The process comprises: (a) extraction with a two-phase solvent system in which the extracting phase is a concentrated anhydrous cuprous nitrate/propionitrile solution, wherein the styrene is selectively complexed with the cuprous ion, and the ethylbenzene countersolvent is a $C_5$ to $C_{18}$ paraffin; and (b) separation of the propionitrile solution phase containing the styrene-cuprous ion complex to recover the styrene therefrom.

U.S. Pat. No. 3,904,484 (King) describes a multi-stage distillation which involves fractionally distilling the dehydrogenation reaction effluent under subatmospheric pressure in a multistage distillation unit comprising a plurality of distillation stages to separately recover styrene monomer, unreacted ethylbenzene and by-product styrene tar residue comprising styrene polymers, $C_{9+}$ aromatic hydrocarbons and polymerization inhibitors. The improvement claimed for this process involves recycling previously recovered styrene tar residue to the dehydrogenation reaction effluent at a point upstream of the separation of the styrene monomer and ethylbenzene so is to maintain a liquid volume ratio of 1 to 20 volumes of styrene tar residue to 20 to 1 volumes of reaction effluent, and distilling the dehydrogenation reaction effluent in the presence of the recycled styrene tar residue.

Others have recovered the overhead condensing duty (thermal energy) from the ethylbenzene/styrene distillation column by using it to boil an ethylbenzene/water azeotrope, for example in U.S. Pat. No. 4,628,136 (Sardina). Such a method requires a large heat transfer area and the use of a falling film evaporator, both of which require costly capital investments and entail costly maintenance. This method also links the dehydrogenation reaction section of the operation directly to the ethylbenzene/styrene splitter, which may not be desirable because upsets in the distillation section could result in difficulty in controlling the reactor section of this system and also could cause damage to the dehydrogenation catalyst.

All of the foregoing prior art processes for separating styrene product from unreacted ethylbenzene following a dehydrogenation reaction therefore have various disadvantages and drawbacks. High costs are incurred due to equipment requirements, maintenance and operating expenses in these prior art processes. These and other drawbacks with and limitations of the prior art processes are overcome, in whole or in part, with the cascade reboiling apparatus and process of this invention.

OBJECTS OF THE INVENTION

Accordingly, a general object of this invention is to provide improved apparatus and process for separating ethylbenzene from styrene monomer.

A principal object of this invention is to provide apparatus and process for significantly reducing the utility costs associated with the normally energy intensive unit operation of distillation separation of ethylbenzene and styrene.

A specific object of this invention is to provide an efficient and economical approach to separating styrene product from other components of the output stream coming from an ethylbenzene dehydrogenation.

Another specific object of this invention is to provide apparatus and process for splitting an ethylbenzene/styrene feed into two process streams for separate distillation processing under different process conditions in an integrated, cascaded operation whereby thermal energy from a first distillation column can be efficiently utilized as thermal input to the second distillation column.

It is also an object of this invention to provide a relatively easy and low cost adaptation for existing styrene plants to increase operating efficiency and reduce energy consumption.

Other objects and advantages of the present invention will in part be obvious and will in part appear hereinafter. The invention accordingly comprises, but is not limited to, the processes and related apparatus, involving the several steps and the various components, and the relation and order of one or more such steps and components with respect to each of the others, as exemplified by the following description and the accompanying drawing. Various modifications of and variations on the process and apparatus as herein described will be apparent to those skilled in the art, and all such modifications and variations are considered within the scope of the invention.

SUMMARY OF THE INVENTION

In general, this invention comprises a cascaded arrangement of two distillation columns and a split feed stream going to those columns whereby heat contained in the overhead vapor stream of one column is utilized to reboil the bottoms of the second column. More specifically, this invention is directed to apparatus and process for splitting a feed containing ethylbenzene and styrene monomer into two process streams for separate distillation respectively in two columns operated at different pressures whereby the high-pressure column is able, by the step of condensing overhead from the high-pressure column, to supply heat to the low-pressure column. The resultant synergisms in process integration and thermal efficiency result in substantially lower energy costs as well as other related savings.

DETAILED DESCRIPTION OF PREFERRED EMBODIMENTS

Figure 1:
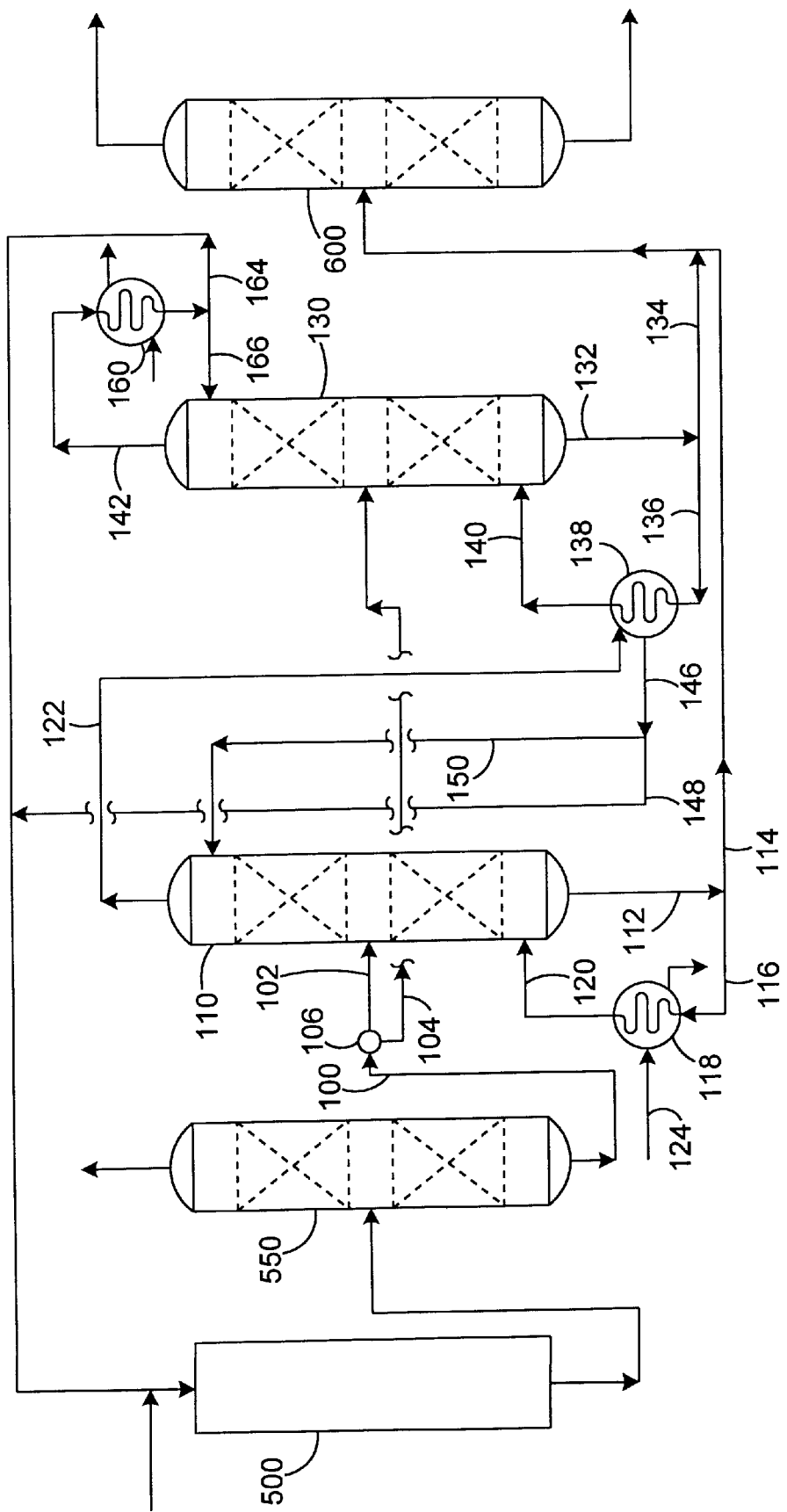
FIG. 1 is a schematic process flow chart illustrating a typical embodiment of the present invention.

As shown in FIG. 1, feed stream 100, typically from an upstream ethylbenzene dehydrogenation unit, shown schematically as unit 500, and consisting essentially of styrene monomer and unreacted ethylbenzene, is divided into two process streams 102 and 104 respectively each being of identical composition and temperature at a fluid divider means such as T-junction 106. Valve or other means associated with T-junction 106 may be utilized to control and adjust the relative proportions of feed 100 directed respectively to process streams 102 and 104. Depending on various process parameters as hereinafter described, the relative proportions of feed 100 directed to process streams 102 and 104 may range from about 90:10 to about 10:90 by volume, preferably a range of about 60:40 to about 40:60. A preferred split of feed 100 consistent with one typical set of commercial operating parameters comprises directing about 47% to process stream 102 and, correspondingly, 53% to process stream 104.

As shown in FIG. 1, process stream 102 is fed to a middle region of high-pressure distillation column 110. High-pressure column 110 is operated under process conditions wherein the lower region of column 110 is at a pressure of about 5–9 psia and a temperature of about 110°–130° C., and the upper region of column 110 is at a pressure of about 4–7 psia and a temperature of about 90°–110° C. In general, condensing and boiling temperatures of the various streams within the distillation section are determined by operating pressure and stream compositions. From a practical point of view, the product compositions are more or less fixed, and column pressure is the only independent variable. Bottoms stream 112 from column 110, comprising predominantly styrene monomer of about 90–96% purity, is divided into a product stream 114 (which is sent to a finishing operation for further purification) and a recycle stream 116. Recycle stream 116 is passed through reboiler 118, where it is heated by thermal exchange with a reboiler heating stream 124, typically steam, and returned by reboiler output stream 120 to the lower region of column 110. The proportion of bottom stream 112 withdrawn for finishing relative to the proportion recycled may range from about 10% to nearly 100%, more typically 20–30%, depending on other process parameters.

Overhead stream 122 from column 110 comprises predominantly ethylbenzene at a temperature higher than the operating conditions, in particular the bottoms temperature, in the second, low-pressure column 130. Thermodynamically, the temperature of the stream supplying the heat must be at a higher temperature than the stream which is absorbing the heat. In commercial practice, the temperature difference between the two integrated fluids must be at least 8 to 10° C. In this case, the temperature of stream 122 is typically in the range of about 90°–110° C., whereas the temperature of the bottoms stream 132 from the low-pressure column 130 is typically in the range of about 70°–95° C. Accordingly, stream 122 can be efficiently utilized in reboiler 138, associated with column 130, as a reboiler heating stream and a source of thermal energy required for operating the low-pressure distillation column, as hereinafter described. Following the heat exchange in reboiler 138, reboiler outlet stream 146, predominantly ethylbenzene at a somewhat reduced temperature relative to stream 122, is divided into an ethylbenzene product stream 148, which may be recycled to the upstream dehydrogenation unit 500 as shown in FIG. 1, and a reflux stream 150 which is returned to the upper region of column 110.

Process stream 104, the second portion of the divided feed 100, is fed to a middle region of low-pressure distillation column 130. Low pressure column 130 is operated under process conditions wherein the lower region of column 130 is at a pressure of about 1–3 psia and a temperature of about 70°–95° C., and the upper region of column 130 is at a pressure of about 0.4–1.5 psia and a temperature of about 40–70° C. Bottoms stream 132 from column 130, comprising predominantly styrene monomer of about 90–96% purity, is divided into a product stream 134 (which is typically combined with styrene stream 114 and sent to a finishing operation such as downstream column 600) and a recycle stream 136. Recycle stream 136 is passed through reboile 138, where it is heated by thermal exchange with ethylbenzene stream 122, as described above. Reboiler unit 138 includes condensing and heat exchange elements such that ethylbenzene stream 122 is cooled and at least partially condensed to liquid form as it passes through reboiler 138, in turn providing heat to recycle stream 136. Heated recycle stream 136 emerges from reboiler 138 and is returned as reboiler output stream 140 to the lower region of column 130. The proportion of bottom stream 132 withdrawn for finishing relative to the proportion recycled may range from about 10% to nearly 100%, more typically 20–30%, depending on other process parameters.

Overhead stream 142 from column 130 comprises predominantly ethylbenzene at a temperature of about 40°–70° C. Stream 142 may be cooled in a condenser 160 using a flow of cooling water 162, and thereafter split into an ethylbenzene product stream 164, which may be recycled as shown in FIG. 1 to the upstream dehydrogenation unit 500, and a reflux stream 166 which is returned to the upper region of column 130.

The following examples further illustrate the practice and benefits of the present invention.

EXAMPLE 1

This example is based on prior art (not the present invention) technology utilizing a single packed distillation column to separate ethylbenzene from styrene monomer. It is presented here for purposes of subsequent comparison with the results of practicing this invention.

Utilizing a single packed column under typical commercial conditions, between 85 to 100 theoretical stages are required to effect the required separation. Ethylbenzene is taken as an overhead product, while styrene is recovered as the bottoms product. A typical design utilizes a 70 mmHgabs (absolute) overhead pressure and a 145 mmHgabs bottoms pressure. With this pressure profile, the column overhead and bottoms temperature are about 66° C. and 92° C. respectively. Heat is supplied to the column via a thermosyphon type reboiler. Typically low pressure steam, condensing between about 115° C. to 130° C., is used as the heat source. Overhead vapor from the column overhead is condensed either in a cooling water or air fin type heat exchanger. To minimize hydrocarbon losses to the column vacuum system, after condensing, the overhead stream is subcooled, typically to between about 40° C. to 50° C. To further prevent hydrocarbons from entering the vacuum system, the column is also equipped with a vent condenser which cools/condenses most of the remaining overhead vapor stream to about 10° C.

With the above described system, for a plant designed to produce 500,000 mta (metric tons/annum) of styrene product, the required heat input to the column is 28.5 million kcal/hr (113 mmBtu/hr). The utilities required to support this separation is roughly 54,300 kg/hr steam and a cooling water circulation flow of 2,970 cubic meters/hr. Representative selective simulation column stage data corresponding to this example is given below in Table I:

TABLE I

| Stage # | Temp. °C. | Press psia | Flow from Stage in kgmol/hr. | | Feed |
|---|---|---|---|---|---|
| | | | Vapor | Liquid | |
| 93*5 | 10.0 | 0.870 | — | 5.8 | |
| 92*4 | 45.0 | 1.064 | 12.4 | 2451.7 | |
| 91*3 | 65.5 | 1.354 | 2837.3 | 2684.0 | 6.0*1 |
| 90 | 66.2 | 1.370 | 3063.7 | 2682.6 | |
| 65 | 76.9 | 1.773 | 3014.2 | 3506.9 | 994.1*2 |
| 4 | 91.6 | 2.755 | 2939.4 | 3555.0 | |
| 3 | 91.8 | 2.772 | 2940.6 | 3556.2 | |
| 2 | 91.9 | 2.788 | 2941.7 | 3553.8 | |
| 1 | 92.4 | 2.804 | 2939.3 | — | |

*1feed stream to Stage 91 = 6.0 kgmol/hr. (air leakage)
*2feed stream to Stage 65 = 994.1 kgmol/hr.
*3vapor stream overhead from Stage 91 = 2837.3 kgmol/hr.
*4liquid stream from Stage 92 = 379.0 kgmol/hr.
vapor stream vent from Stage 92 = 12.4 kgmol/hr.
*5vapor stream from Stage 93 = 6.7 kgmol/hr.
Bottoms stream = 614.4 kgmol/hr.
Internal reflux ratio = 7.1
Heat Input Required to Column = 28.506 million kcal/hr.
Stage 93 represents the Vent Condenser
Stage 92 represents the Main Condenser
Stage 91 represents the top of the column
Stage 1 represents the reboiler draw

EXAMPLE 2

This example is based on a representative embodiment of the present invention as shown in FIG. 1 wherein a mixed feed comprising ethylbenzene and styrene monomer is split into two process streams for distillation respectively in two cascaded distillation columns operated under different pressure and temperature conditions. The pressures of the columns are set such that the overhead condensing temperature of one column is higher than the bottoms temperature of the other. Because the overhead vapor from the high-pressure column condenses at a temperature higher than the bottoms temperature of the low-pressure column, this vapor stream can be used as the heat source to the low-pressure column, resulting in surprising process efficiencies and synergisms.

In this example of the present invention, the low-pressure column operates with an overhead pressure of 36 mmHgabs (0.677 psia) and a bottoms pressure of 100 mmHgabs (1.934 psia). At this bottoms pressure, the boiling point of the bottoms liquid mixture is 82.6° C. The high-pressure column operates with an overhead pressure of 290 mmHgabs (5.704 psia) and a bottoms pressure of 365 mmHgabs. At this operating pressure, the overhead vapor from the high-pressure column condenses at 101.7° C., which is sufficiently above the bottoms temperature of the low-pressure column (82.6° C.) for purposes of this invention. Because adequate thermal driving force is available, the higher pressure overhead can be used to reboil the bottoms recycle stream from the low-pressure column. With this scheme, heat is cascaded from one column system to the other. In this example, the total feed flow is split such that 47% of the feed is directed to the high-pressure column. The split of feed between the columns is established such that the high-pressure overhead condensing duty matches the reboiling duty of the low-pressure column. The only heat supplied to this two-column system is via the reboiler of the high-pressure column, at the rate of 16.58 mmkcal/hr (65.9 mmBtu/hr). Likewise, the only significant heat removal step in this two-column system is from the condenser of the low-pressure column. The estimated utility consumptions for the integrated system are 31,600 kg/hr stream input and 1,500 m3/hr of cooling water circulation. This represents a 40% savings in steam consumption and approximately a 50% saving in cooling water circulation as compared with the respective heating and cooling requirements for Example 1.

Representative selective simulation column stage data for the low-pressure and high-pressure columns corresponding to this example are given below in Tables II-A (Low-Pressure) and II-B (High-Pressure):

TABLE II-A (Low-Pressure)

| Stage # | Temp. ° C. | Press psia | Flow from Stage in kgmol/hr. | | Feed |
|---|---|---|---|---|---|
| | | | Vapor | Liquid | |
| 93[*5] | 10.0 | 0.387 | — | 12.9 | |
| 92[*4] | 37.8 | 0.483 | 17.8 | 1268.1 | |
| 91[*3] | 50.0 | 0.677 | 1473.4 | 1332.5 | 3.8[*1] |
| 90 | 50.8 | 0.691 | 1534.1 | 1331.8 | |
| 65 | 64.3 | 1.040 | 1512.0 | 1739.0 | 524.1[*2] |
| 4 | 81.7 | 1.892 | 1449.9 | 1773.1 | |
| 3 | 81.9 | 1.906 | 1450.6 | 1773.8 | |
| 2 | 82.1 | 1.920 | 1451.3 | 1772.9 | |
| 1 | 82.6 | 1.934 | 1450.4 | — | |

[*1]feed stream to Stage 91 = 3.8 kgmol/hr. (air leakage)
[*2]feed stream to Stage 65 = 524.1 kgmol/hr.
[*3]vapor stream overhead from Stage 91 = 1473.4 kgmol/hr.
[*4]liquid stream from Stage 92 = 200.5 kgmol/hr.
vapor stream vent from Stage 92 = 17.8 kgmol/hr.
[*5]vapor stream from Stage 93 = 4.8 kgmol/hr.
Bottoms stream = 322.5 kgmol/hr.
Internal reflux ratio = 6.6
Heat Input Required to Low-Pressure Column (from the High-Pressure Column) = 14.270 million kcal/hr.

TABLE II-B (High-Pressure)

| Stage # | Temp. ° C. | Press psia | Flow from Stage in kgmol/hr. | | Feed |
|---|---|---|---|---|---|
| | | | Vapor | Liquid | |
| 93[*5] | 10.0 | 5.318 | — | 148.9 | |
| 92[*4] | 101.7 | 5.511 | 152.8 | 1610.4 | |
| 91[*3] | 103.9 | 5.704 | 1787.1 | 1626.3 | 3.8[*1] |

TABLE II-B-continued (High-Pressure)

| Stage # | Temp. ° C. | Press psia | Flow from Stage in kgmol/hr. | | Feed |
|---|---|---|---|---|---|
| | | | Vapor | Liquid | |
| 90 | 104.3 | 5.719 | 1799.2 | 1626.7 | |
| 65 | 111.1 | 6.095 | 1764.0 | 2085.1 | 464.8[*2] |
| 4 | 119.4 | 7.013 | 1787.9 | 2080.1 | |
| 3 | 119.5 | 7.028 | 1788.2 | 2080.3 | |
| 2 | 119.6 | 7.043 | 1788.5 | 2077.7 | |
| 1 | 120.0 | 7.058 | 1785.8 | — | |

[*1]feed stream to Stage 91 = 3.8 kgmol/hr. (air leakage)
[*2]feed stream to Stage 65 = 464.8 kgmol/hr.
[*3]vapor stream overhead from Stage 91 = 1787.1 kgmol/hr.
[*4]liquid stream from Stage 92 = 172.8 kgmol/hr.
vapor stream vent from Stage 92 = 152.8 kgmol/hr.
[*5]vapor stream from Stage 93 = 3.9 kgmol/hr.
Bottoms stream = 291.9 kgmol/hr.
Internal reflux ratio = 9.4
Heat Input Required to Column = 16.580 million kcal/hr.

EXAMPLE 3

As previously discussed, in styrene monomer (SM) plants which dehydrogenate ethylbenzene (EB) to styrenie, the reactant ethylbenzene feed is typically converted at a rate of 50 to 70% per pass across the reactor. The unireacted ethylbenlzene must then be recovered and separated from the styrene product prior to recycle to the reaction system. In the reaction section, components lighter than EB and components heavier than styrene are also produced. This mixture of light components, etlhylbenizene, styrene and heavies is typically fed to a distillation train for SM product purification and EB recovery. The general practice is to accomplish these purifications by a three-step distillation.

To separate the above components, the distillation section of a styrene plant typically consists of three independent column systems. The first column in the series recovers the light components such as benzene and toluene (B/T Column) shown schematically in FIG. 1 as column 550; the second column recovers unreacted ethylbenzene (EB/SM Column); and the last column distills heavies from the finished styrene product (Finishing Column) shown schematically in FIG. 1 as column 600.

This typical three-column series in the distillation section of a styrene plant provides a further opportunity to demonstrate the surprising and completely unexpected advantages of the present invention in comparison with possible alternative cascade reboiler configurations which may superficially appear similar to that of the present invention but which lead to very different cost and energy efficiency results.

Examples 3 and 4 illustrate the effect of applying the general concept of cascading energy from one column system to another in the conventional three-column series used in the distillation section of a styrene plant but without the novel concept of this invention of splitting the EB/SM stream into two process streams for separate distillation in two cascaded EB/SM distillation columns. For purposes of example 3, the conventional three-column series is adapted to cascade the heat from the overhead vapor of the ethylbenzene/styrene (EB/SM) column (the middle column in the conventional series) to the final column which removes heavies (Finishing Column).

Heat is typically supplied to the finishing column via two independent reboilers. The first, larger reboiler, which provides the majority of the column's heat input, typically operates at low temperature, while the second, smaller reboiler supplies heat at a much higher temperature. The higher temperature service is required to strip heavy polymers from the desired styrene monomer. To effectively strip the polymers from styrene, the high temperature stripping is usually accomplished at temperature of about 130° C. At this elevated temperature, cascade reboiling of the residue stripping reboiler with other streams within the styrene distillation is not practical. However, the larger, low-temperature reboiler of the finishing column is a candidate for adaption for cascade reboiling. For example, normally the two columns under consideration (the EB/SM and finishing columns) might have the following, operating characteristics:

| Standard Operating Characteristics | | |
|---|---|---|
| | EB/SM Column | Finishing Column |
| Overhead Condensing Temperature (° C.) | 45 | 45 |
| Overhead Pressure (psia) | 1.354 | 0.773 |
| Bottoms Temperature (° C.) | 93 | 98 |
| System Heat Input (mmkcal/hr) | 7.3 | 3.4 |

The total heat input required by this two-column system is 10.7 mmkcal/hr (7.3+3.4). The heat input to the finishing column includes both the high and low temperature sources. To achieve sufficient thermal driving force to reboil the finishing column with the overhead vapor of the EB/SM column, the pressure of the EB/SM column must be increased and the pressure of the finishing column must be decreased. Given the same feed rate and product compositions as the standard case above, one feasible set of operating conditions for the Example 3 cascade reboiling adaptation is illustrated below:

| Cascade Reboiling Adaptation | | |
|---|---|---|
| | EB/SM Column | Finishing Column |
| Overhead Condensing Temperature (° C.) | 105 | 38 |
| Overhead Pressure (psia) | 6.575 | 0.580 |
| Bottoms Temperature (° C.) | 123 | 96 |
| System Heat Input (mmkcal/hr) | 8.9 | 3.3 |
| Recoverable Low Temp Heat (mmkcal/hr) | — | 2.8 |

In this case, the overhead vapor of the EB/SM column is used to reboil the finishing column bottoms. A portion of the overhead vapor stream is condensed in the finishing column's reboiler located at the bottom of the tower. The balance of the vapor from the EB/SM column not used in the cascade reboiling is directed to a cooling water condenser. At the above operating conditions, the differential temperature available for cascade reboiling is approximately 9° C. (105–96). The net amount heat supplied to the columns with this scheme is 9.4 mmkcal/hr (8.9+3.3−2.8).

At the required higher operating pressure of the EB/SM column, the relative volatilities of the two key components, ethylbenzene and styrene, are reduced such that 20% more energy is required to achieve the same degree of fractionation as the standard design (7.3 versus 8.9 mmkcal/hr). While this cascade reboiling adaptation on one hand recovers energy from the EB/SM column by cascading it to the finishing column, conversely the need to operate the EB/SM column at higher pressure increases the required energy input. Overall, for this example, cascade reboiling saves about 1.3 mmkcal/hr. Based on current energy prices, this translates into an energy cost savings of about $100,000/year.

Operating the EB/SM column at higher pressure and temperature, however, requires that the rate of polymerization inhibitor addition be increased significantly. At the higher temperatures required by the cascade reboiling adaptation, the styrene polymerization rate of the EB/SM column is 7 to 8 times higher than the standard (non-cascade reboiling) case. For example, if the polymerization inhibitor dosing rate is doubled, the increased cost of the inhibitor would be approximately equal to the total projected energy cost savings from cascade reboiling. Moreover, under these conditions, one would expect that the yield loss to heavies and polymer to also increase. Therefore, evaluating this Example 3 adaptation in its entirety, one would conclude that the increased cost of inhibitor negates all of the projected energy cost savings of this scheme. Furthermore, given that cascade reboiling inherently increases capital investment, compared to the standard design, the payout of this cascade reboiling adaptation clearly would not meet commonly applied thresholds needed to justify energy recovery programs. Accordingly, Example 3 would teach those skilled in this art away from attempting to integrate cascade reboiling technology into the conventional EB/SM distillation system.

EXAMPLE 4

A second possible cascade reboiling adaptation of the conventional EB/SM distillation system comprises reboiling of the first column in the distillation train (B/T Column) with the EB/SM overhead vapor. The heat duty of the first column (benzene/toluene removal column) represents only 10% of the total energy supplied to the distillation section. Given the relatively small heating requirements of the B/T Column, additional investment cannot typically be justified to support cascade reboiling of this service. Moreover, because the feed stream to this initial column contains dissolved light gases, lowering the pressure of this column is usually not practical. Reducing the pressure of this column results in a larger increase in hydrocarbon losses to the column's vacuum system. With the normal bottoms temperature of the B/T column being around 100° C., cascade reboiling is difficult unless the heat source is on the order of 108 to 110° C. Again, having to operate the EB/SM column with this elevated overhead temperature results in a significant increase in styrene polymerization rate. Similar to the finishing column adaptation described previously in Example 3, the cost of increased polymerization inhibitor would negate any energy savings. Again, based on economics, cascade reboiling of the benzene/toluene column with the EB/SM column overhead cannot be justified under normal circumstances. As with Example 3, Example 4 would teach those skilled in this art away from attempting to integrate cascade reboiling technology into the conventional EB/SM distillation system.

It will be apparent to those skilled in the art that other changes and modifications may be made in the above-described apparatus and process without departing from the scope of the invention herein, and it is intended that all matter contained in the above description shall be interpreted in an illustrative and not in a limiting sense. More specifically, although the various embodiments of this invention have been described with reference to the separation of ethylbenzene from styrene monomer as part of an overall styrene plant which produces styrene by dehydrogenation of ethylbenzene, the apparatus and processes described herein may have similarly beneficial application to other mixtures ethylbenzene and styrene as well as to the separation of other hydrocarbon mixtures wherein the components have volatilities that are relatively close to one another resulting in difficult distillation separations.

Having described the invention, what is claimed is:

1. An apparatus for the distillation separation of a first hydrocarbon compound from a hydrocarbon mixture consisting essentially of said first hydrocarbon compound and a second hydrocarbon compound, the boiling points of which are so close as to make separation by fractional distillation difficult, said apparatus comprising:

(a) first and second distillation column means, each for distilling respectively first and second portions of said hydrocarbon mixture under different pressure and temperature conditions, wherein one of said distillation column means comprises a higher-pressure distillation column and an associated thermal energy source and the other distillation column means comprises a lower-pressure distillation column and an associated thermal energy source;

(b) a T-junction splitter for splitting a stream of said hydrocarbon mixture into said first and second portions, said first and second portions being of identical composition and temperature;

(c) first and second conduits for conveying respectively said first and second portions respectively to the distillation columns of said first and second distillation column means;

(d) a third conduit for conveying a higher-pressure distillation column overhead stream withdrawn from an upper region of the higher-pressure distillation column to a thermal exchange location;

(e) thermal exchange means at said thermal exchange location whereby said higher-pressure distillation column overhead stream is brought into thermal exchange with a lower-pressure distillation column bottoms stream withdrawn from a lower region of the lower-pressure distillation column so as to produce a heated lower-pressure distillation column bottoms stream; and, (f) means for returning said heated lower-pressure distillation column bottoms stream to the lower-pressure distillation column.

2. An apparatus according to claim 1 wherein said T-junction splitter further comprises flow control means to control the relative proportions of said first and second portions.

3. An apparatus according to claim 1 wherein said thermal exchange means at said thermal exchange location comprises a reboiler.

4. An apparatus according to claim 1 wherein the thermal energy source associated with each distillation column comprises a reboiler.

5. An apparatus according to claim 1 further comprising a fourth conduit for returning at least a portion of said higher-pressure distillation column overhead stream from said thermal exchange location to the higher-pressure distillation column.

6. A system for producing purified styrene monomer from an ethylbenzene feed by dehydrogenation and subsequent separation, said system comprising:

(a) a dehydrogenation reactor packed with a dehydrogenation catalyst and having a dehydrogenation reactor inlet and a dehydrogenation reactor outlet;

(b) a fluid divider in-line with said dehydrogenation reactor outlet for dividing an effluent stream from said dehydrogenation reactor outlet into first and second portions, said first and second portions being of identical composition and temperature;

(c) a first conduit in communication with said fluid divider for conveying said first portion to a first distillation column;

(d) a second conduit in communication with said sulfide for conveying said second portion to a second distillation column;

(e) cascade reboiler means associated with said second distillation column said cascade reboiler means including: means for withdrawing a second-column bottoms stream from a lower region of said second distillation column; means for passing the second column bottoms stream in thermal contact with a fluid stream at a higher temperature to produce a heated second-column bottoms stream; and means for thereafter returning said heated bottoms stream to said second distillation column; and (f) a third conduit for conveying a first-column overhead stream from an upper region of said first distillation column to said cascade reboiler means to function as said fluid stream at a higher temperature.

7. A system according to claim 6 further comprising a third distillation column, located inline between said dehydrogenation reactor and said fluid divider, for separating styrene and ethylbenzene from the lighter components of the dehydrogenation reactor effluent.

8. A system for producing purified styrene monomer from an ethylbenmene feed by dehydrogenation and subsequent separation, said system comprising:

(a) a dehydrogenation reactor packed with a dehydrogenation catalyst and having a dehydrogenation reactor inlet and a dehydrogenation reactor outlet;

(b) a fluid divider inline with said dehydrogenation reactor outlet for dividing an effluent stream from said dehydrogenation reactor outlet into first and second portions, said first and second portions being of identical composition and temperature;

(c) a first conduit in communication with said fluid divider for conveying said first portion to a first distillation column;

(d) a second conduit in communication with said fluid divider for conveying said second portion to a second distillation column;

(e) cascade reboiler means associated with said second distillation column, said cascade reboiler means including: means for withdrawing a second-column bottoms stream from a lower region of said second distillation column; means for passing the second column bottoms stream in thermal contact with a fluid stream at a higher temperature to produce a heated second-column bottoms stream; and means for thereafter returning said heated bottoms stream to said second distillation column;

(f) a third conduit for conveying a first-column overhead stream from an upper region of said first distillation column to said cascade reboiler means to function as said fluid stream at a higher temperature;

(g) a third distillation column, located in-line between said dehydrogenation reactor and said fluid divider, for separating styrene and ethylbenzene from the fighter components of said effluent stream; and, (h) a fourth distillation column located in-line downstream from said first and second distillation columns for separating styrene monomer from heavier hydrocarbon components.

9. A system for producing purified styrene monomer from an ethylbenzene feed by dehydrogenation and subsequent separation, said system comprising:

(a) a dehydrogenation reactor packed with a dehydrogenation catalyst and having a dehydrogenation reactor inlet and a dehydrogenation reactor outlet;

(b) a fluid divider in-line with said dehydrogenation reactor outlet for dividing an effluent stream from said dehydrogenation reactor outlet into first and second portions, said first and second portions being of identical composition and temperature, wherein said fluid divider includes flow control means to control the relative proportions of said first and second portions;

(c) a first conduit in communication with said fluid divider for conveying said first portion to a first distillation column;

(d) a second conduit in communication with said fluid divider for conveying said second portion to a second distillation column;

(e) cascade reboiler means associated with said second distillation column, said cascade reboiler means including; means for withdrawing a second column bottoms stream from a lower region of said second distillation column; means for passing the second column bottoms stream in thermal contact with a fluid stream at a higher temperature to produce a heated second-column bottoms stream, and means for thereafter returning said heated bottoms stream to said second distillation column; and, (f) a third conduit for conveying a first-column overhead stream from an upper region of said first distillation column to said cascade reboiler means to function as said fluid stream at a higher temperature.

10. A system for producing purified styrene monomer from an ethylbenzene feed by dehydrogenation and subsequent separation, said system comprising:

(a) a dehydrogenation reactor packed with a dehydrogenation catalyst and having a dehydrogenation reactor inlet and a dehydrogenation reactor outlet;

(b) a fluid divider in-line with said dehydrogenation reactor outlet for dividing an effluent stream from said dehydrogenation reactor outlet into first and second portions, said first and second portions being of identical composition and temperature;

(c) a first conduit in communication with said fluid divider for conveying said first portion to a first distillation column;

(d) a second conduit in communication with said fluid dider for conveying said second portion to a second distillation column;

(e) cascade reboiler means associated with said second distillation cole said cascade reboiler means including: means for withdrawing a second-column bottoms stream from a lower region of said second distillation column; means for passing the second column bottoms stream in thermal contact with a fluid stream at a higher temperature to produce a heated second-column bottoms stream, and means for thereafter returning said heated bottoms stream to said second distillation column;

(f) a third conduit for conveying a first-column overhead stream from an upper region of said first distillation column to said cascade reboiler means to function as said fluid stream at a higher temperature; and, (g) a fourth conduit for returning a first portion of said overhead stream coming from said cascade reboiler means as a reflux stream to said first distillation column.

11. A system for producing purified styrene monomer from an ethylbenzene feed by dehydrogenation and subsequent separation, said system comprising:

(a) a dehydrogenation reactor packed with a dehydrogenation catalyst and having a dehydrogenation reactor inlet and a dehydrogenation reactor outlet;

(b) a fluid divider in-line with said dehydrogenation reactor outlet for dividing an effluent stream from said dehydrogenation reactor outlet into first and second portions, said first and second portions being of identical composition and temperature;

(c) a first conduit in communication with said fluid divider for conveying said first portion to a first distillation column;

(d) a second conduit in communication with said fluid divider for conveying said second portion to a second distillation column;

(e) cascade reboiler means associated with said second distillation column, said cascade reboiler means including: means for withdrawing a second-column bottoms stream from a lower region of said second distillation column mews for passing the second column bottoms stream in thermal contact with a fluid stream at a higher temperature to produce a heated second-column bottoms stream; and means for thereafter returning said heated bottoms stream to said second distillation column;

(f) a third conduit for conveying a first-column overhead stream from an upper region of said first distillation column to said cascade reboiler means to function as said fluid stream at a higher temperature;

(g) a fourth conduit for returning a first portion of said overhead stream coming from said cascade reboiler means as a reflux stream to said first distillation column; and, (h) a fifth conduit for recycling a second portion of said overhead stream coming from said cascade reboiler means as a recycle stream to said dehydrogenation reactor.

* * * * *

UNITED STATES PATENT AND TRADEMARK OFFICE
CERTIFICATE OF CORRECTION

PATENT NO.  : 6,171,449 B1
DATED       : January 9, 2001
INVENTOR(S) : Vincent A. Welch Page 1 of 1

It is certified that error appears in the above-identified patent and that said Letters Patent is hereby corrected as shown below:

Column 12,
Line 9, delete "sulfide" and substitute therefore -- fluid divider --.
Line 13, after "column" insert a comma -- , --.
Line 27, rewrite "inline" as -- in-line --.
Line 32, rewrite "ethylbenmene" as -- ethylbenzene --.
Line 37, rewrite "inline" as -- in-line --.
Line 64, rewrite "fighter" as -- lighter --.

Column 13,
Line 26, change the semicolon ";" to a colon -- : --; also, rewrite "second column" as -- second-column --.
Line 53, rewrite "dider" as -- divider --.
Line 56, rewrite "cole" as -- column --.

Column 14,
Line 6, change the comma "," to a semicolon -- ; --.
Line 38, after "column" add a semicolon -- ; --; also, rewrite "mews" as -- means --.

Signed and Sealed this

Second Day of October, 2001

Attest:

NICHOLAS P. GODICI
Attesting Officer    Acting Director of the United States Patent and Trademark Office